United States Patent [19]

Gustafsson

[11] Patent Number: 5,044,767

[45] Date of Patent: Sep. 3, 1991

[54] DEVICE FOR MEASURING THERMAL PROPERTIES OF A TEST SUBSTANCE-THE TRANSIENT PLANE SOURCE (TPS) METHOD

[75] Inventor: Silas Gustafsson, Gothenburg, Sweden

[73] Assignee: Thermetrol AB, Sweden

[21] Appl. No.: 446,935

[22] Filed: Dec. 6, 1989

Related U.S. Application Data

[63] Continuation-in-part of Ser. No. 411,463, Sep. 19, 1989, abandoned.

[30] Foreign Application Priority Data

Mar. 16, 1988 [SE] Sweden .............................. 88009436

[51] Int. Cl.$^5$ ............................................. G01N 25/18
[52] U.S. Cl. ......................................... 374/44; 347/43
[58] Field of Search .............................. 374/44, 43, 12

[56] References Cited

U.S. PATENT DOCUMENTS

| | | |
|---|---|---|
| 4,630,938 | 12/1986 | Piorkowska-Palczewska et al. ........................................ 374/44 |
| 4,841,543 | 6/1989 | Dittmar et al. ........................ 374/44 |
| 4,859,078 | 8/1989 | Bowman et al. ...................... 374/44 |
| 4,861,167 | 8/1989 | Lobo et al. ............................. 374/44 |

OTHER PUBLICATIONS

Gustafsson et al., Journal of Applied Physics 52, Apr. 1981, pp. 2596–2600.
Gustafsson et al., Journal of Physic. D: Applied Physics, vol. 12, 1979, pp. 1411–1421.
Proceedings of 5th Annual ISA Test Measurement Symposium: Advances in Test Measurement, 1968, Hager Jr., pp. 1–6.

Primary Examiner—Thomas B. Will
Assistant Examiner—William C. Dowling
Attorney, Agent, or Firm—Ostrolenk, Faber, Gerb & Soffen

[57] ABSTRACT

A device for measuring thermal properties of a test substance, which device incorporates a thin element or a layer of an electrically conductive material, e.g. metal, intended to be brought in heat conductive contact with said test substance (3), means for passing an electric current through said element or layer for supplying heat to the test substance and causing a temperature increase therein and instrument for recording the voltage variation over the element or layer as a function of time. In order to increase the characteristic time for the experiments and thereby making it possible to use less sophisticated measuring instruments the active part of said element (6) or layer (4) over which the measurement is made has substantially equal size along at least two lateral dimensions. The element can e.g. be given of square or circular shape.

7 Claims, 4 Drawing Sheets

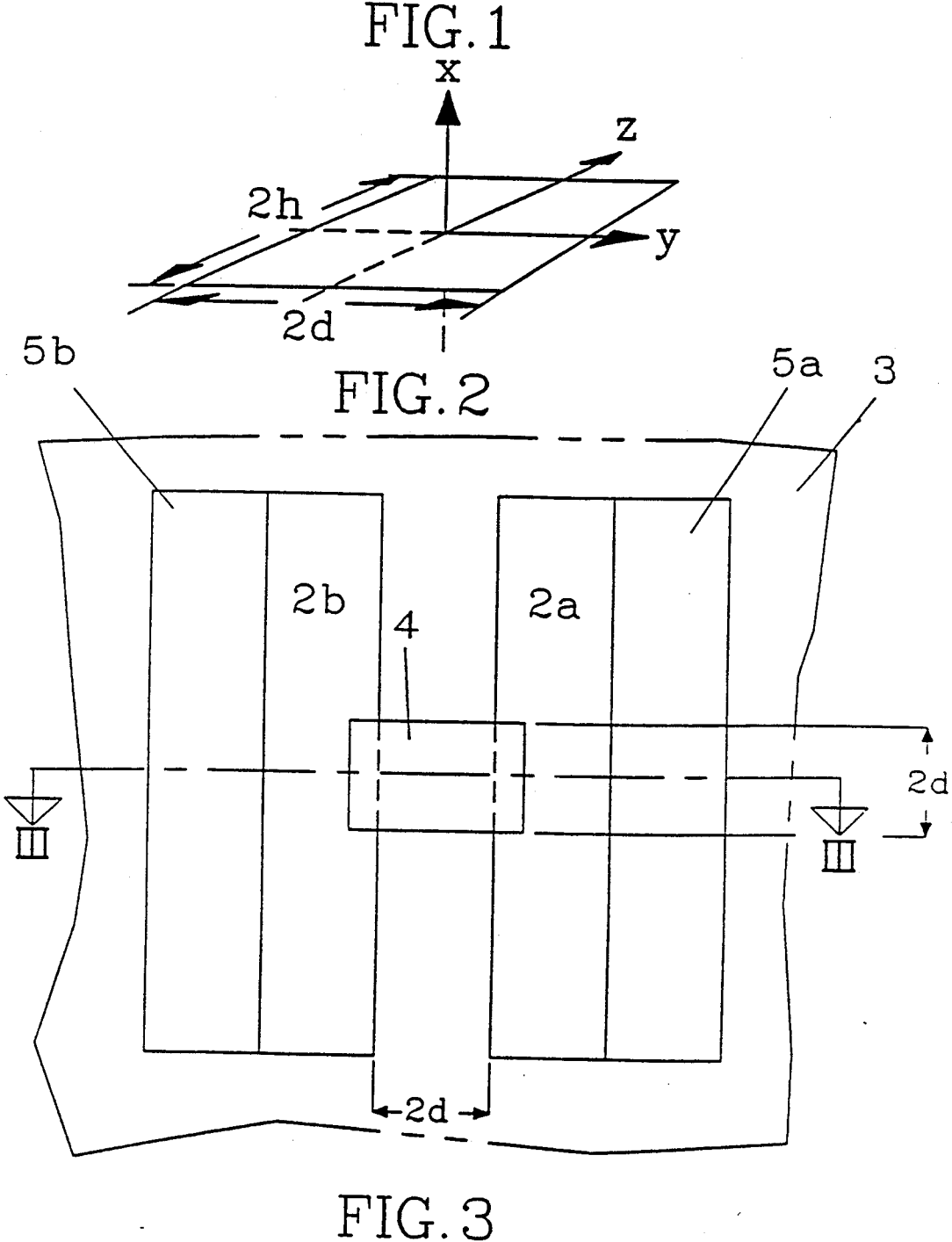

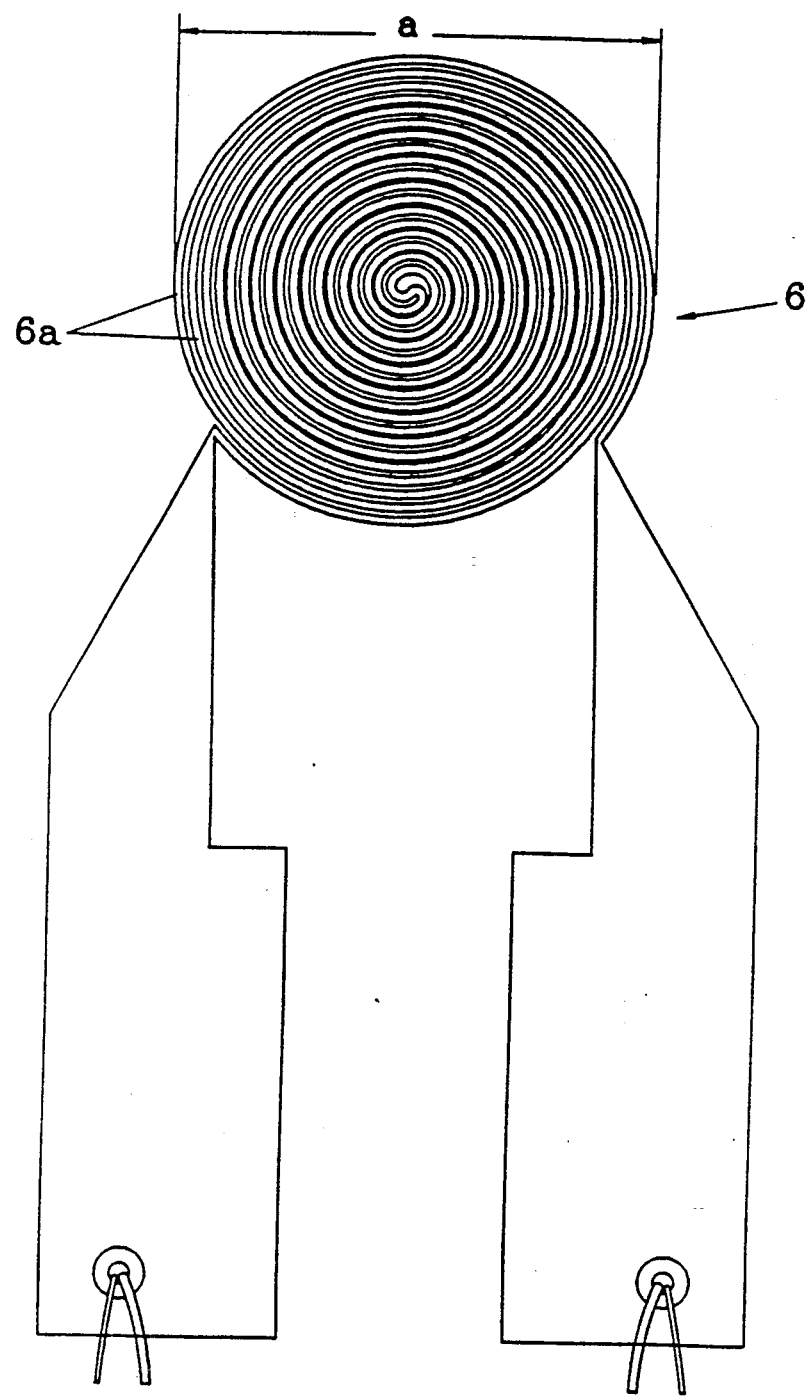

DEVICE FOR MEASURING THERMAL PROPERTIES OF A TEST SUBSTANCE-THE TRANSIENT PLANE SOURCE (TPS) METHOD

This application is a continuation-in-part of U.S. Ser. No. 07/411,463, filed Sept. 19, 1989, now abandoned.

The present invention refers to a device for measuring thermal properties of a test substance, which device incorporates a thin element or layer of an electrically conductive material, e.g. metal, intended to be brought in heat conductive contact with said test substance, means for passing an electric current through said element or layer for supplying heat to the test substance and causing a temperature increase therein and instrument for recording the voltage variation over the element or the layer as a function of time and to evaluate therefrom thermal properties, such as thermal conductivity and diffusivity of the test substance.

BACKGROUND OF THE INVENTION

The technique known as the THS (Transient Hot Strip)-technique for measuring thermal conductivity and diffusivity of a test substance is described in several publications, see for example articles by Gustavsson et al. in J. Phys. D.12.1411 (1979) and J. Appl. Phys. 52,2596 (1981). According to the THS-technique a thin strip of a metal foil is provided between two identical test substances or alternatively a thin metal film is deposited on the test substance by vapour deposition, which metal foil or alternatively metal film acts as an extended plane heat source and as a temperature sensor. A constant current is passed through the metal strip and voltage variations are recorded as a function of time, in accordance with changes in the resistance of the strip. At a certain constant current the voltage variation is mainly dependent on the strip temperature coefficient for the resistance (TCR) and the mean temperature increase of the strip in turn depends on the thermal properties of the test substance. It thereby is possible with such a measurement to estimate the thermal conductivity and diffusivity of the test substance. In order to simplify the models of calculation it is generally presupposed that the length of the strip is infinite. The time characteristic for the experiments is very short as it depends on the square of the strip width, which calls for sensitive measuring instruments, which may be difficult to handle outside laboratory environment and by untrained personnel.

Object and Most Essential Features of the Invention

The object of the present invention is to provide a sensor for transient measurements, which increases the characteristic time for the experiments and which therefore requires less sophisticated measuring instruments, without reducing the accuracy of the measurement. This has been achieved according to the invention therein that the active part of said strip or layer has substantially equal size along at least two lateral dimensions, whereby the geometry of the strip or the layer forms part of the theoretical model upon which the calculation of the thermal properties of the test substance is based. With the new geometry of the Transient Plane Source (TPS) elements the time characteristic for the measurements can typically be increased by two orders of magnitude and the resistance by one order of magnitude as compared with the THS method.

Description of the Drawings

The invention will hereinafter be further described with reference to some embodiments shown in the accompanying drawings.

FIG. 1 illustrates schematically a square strip according to the invention.

FIG. 2 shows in a view from above an embodiment of the invention.

FIG. 3 is a section along line III—III in FIG. 2.

FIG. 7 shows in a view from above a further embodiment of the invention.

Theoretical Background

Figure 4:
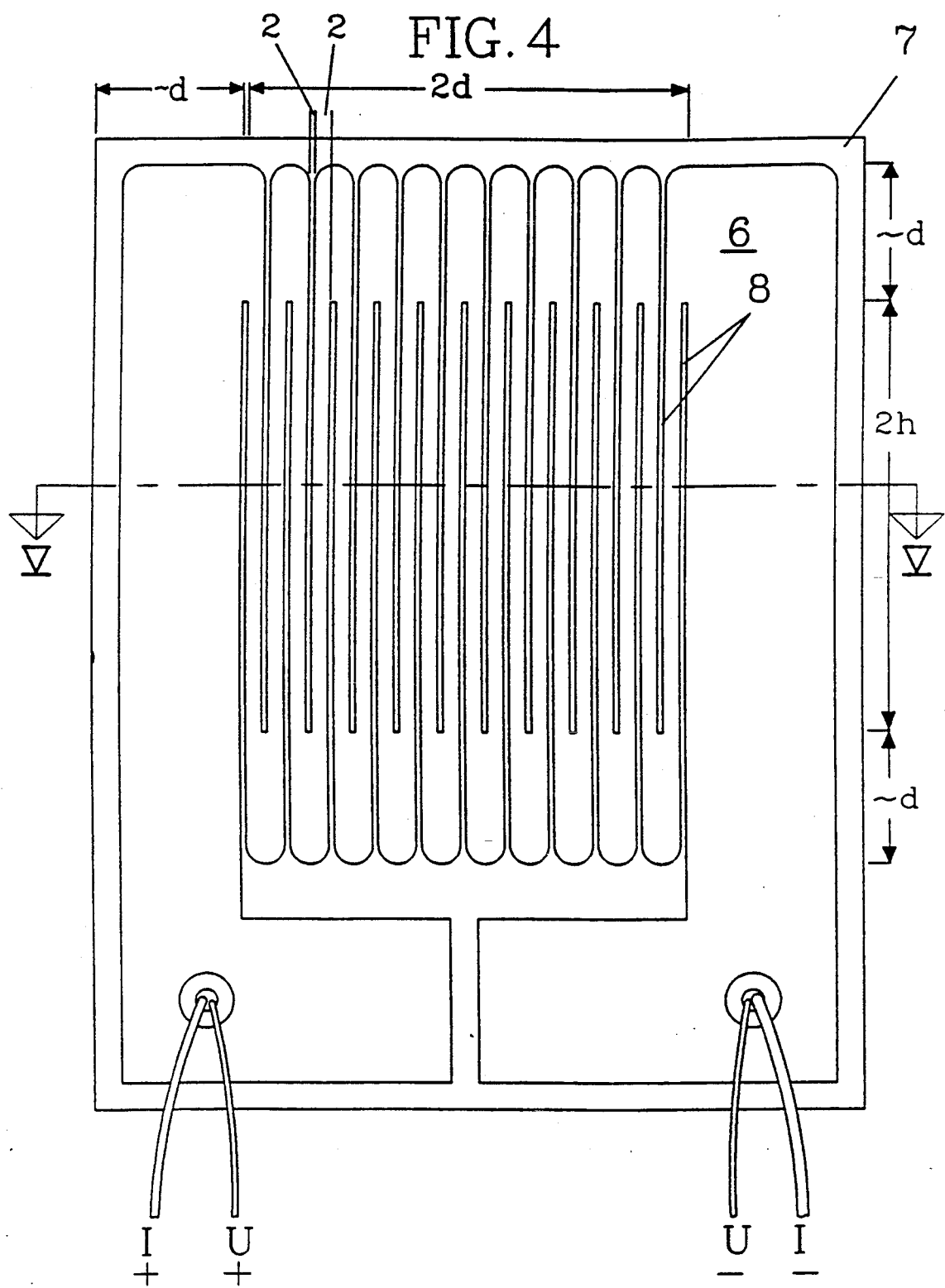
FIG. 4 shows in a view from above a second embodiment of the invention.

Thermal conductivities vary extensively depending on the structure, density, porosity etc., of different materials. Extreme situations that can be mentioned are the thermal conductivity of fine powders with low interstitial gas pressure, which typically is of the order of 0.01 W/mK, while the thermal conductivity of dense single crystals at temperatures around 10° K may be around 10 000 W/mK or even higher.

Because of the large variation of the thermal transport properties, a number of different experimental techniques have been developed for these different materials and different experimental conditions. The introduction of transient hot plane source techniques (Hot Square, Hot Disc etc.) is being made with the specific intention of covering as large ranges of thermal conductivities and thermal diffusivities as possible with the same experimental method.

Maximum applicability as well as convenience is achieved with the proposed experimental methods by the use of resistive elements both as heat sources and as temperature sensors. By recording the voltage increase over the source/sensor element while it is exposed to an essentially constant current pulse, it is possible to get information on the average temperature increase of the element, provided it is made of a material with a suitably high and known TCR (Temperature Coefficient of the Resistivity).

In typical situations the TCR is of the order of 0.001 (1/K) or higher, which means that a mean temperature increase of about one degree of the source/sensor element is sufficient for precise recordings of both the thermal conductivity and the thermal diffusivity.

In a transient and time limited experiment the real time voltage variation of the source/sensor element is recorded while it is exposed to a current which at the end of the transient event might have increased one degree or even less.

The kinds of recordings are identical to those performed when working with the Transient Hot-Strip technique mentioned above. The most convenient electrical recording of the small voltage variations is made with a bridge circuit, which is working progressively off balance. In the references cited a detailed description is also given on how to evaluate the thermal conductivity and thermal diffusivity coefficient from the transient voltage recordings as soon as the theoretical expression of the time evolution of the average temperature, as sensed by the resistive pattern of the thin strips making up the TPS element, is known.

The elements proposed here are designed to remedy two difficulties experienced with the "hot-strip" arrangements, when studying transport properties of solid materials:

a. the length to width ratio of a hot-strip must be such that the initial resistance becomes rather low, which has a negative influence on its sensitivity as a thermal sensor.

b. the ratio $h(kt)^{-\frac{1}{2}}$, where 2h is the strip length, k is the thermal diffusivity and t is the total time of the transient recording, tends to be such that, for samples of convenient laboratory size, the measuring time becomes inconveniently small.

The plane TPS elements proposed here may be given different shapes but their over-all length to width ratio is the same at least within an order of magnitude.

A thin metal layer or a thin metal element in form of a foil, the width of which is approximately equal to its length, and which is in thermal contact with a test substance, is used in a corresponding manner as in the THS-technique. For an infinite isotropic medium which surrounds an element 1 according to FIG. 1 and having the length 2h, the width 2d, a negligible thickness, i.e. negligible heat capacity, and with no thermal disturbance supply from end contacts, the temperature increase $T(y,z,t)$ at each time in dependency of the constantly emitted power per unit of area Q:

$$\Delta T(y,z,t) = \frac{Q}{2\Lambda(\pi)^{3/2}} \int_0^{\sqrt{4kt}} \frac{1}{\sigma^2} \cdot d\sigma \times \\ \times \int_{-d}^{d} dy' \exp\{-(y-y')^2/\sigma^2\} \times \int_{-h}^{h} dz' \exp\{-(z-z')^2/\sigma^2\} \quad (1)$$

where
$\sigma = \sqrt{4k(t-t')}$
$\Lambda$ = Thermal Conductivity of the medium
$k$ = Thermal Diffusivity of the medium
$Q = P_o/4dh$
and
$P_o$ = Power released in the strip The average increase of temperature $\overline{\Delta T(t)}$ in the element at any time t is $$\Delta T(t) = \frac{1}{2d} \cdot \frac{1}{2h} \int_{-d}^{d} dy \int_{-h}^{h} dz \cdot \Delta T(y,z,t)$$

For a square element d=h so that $\overline{\Delta T(t)}$ becomes $$\Delta T(t) = \frac{1}{4d^2} \int_{-d}^{d} dy \int_{-d}^{d} dz \cdot \Delta T(y,z,t) \quad (2)$$

This equation can be solved to give:

$$\Delta T(\tau) = \frac{P_o}{4d\Lambda \sqrt{\pi}} \int_0^{\tau} d\eta [\mathrm{erf}(1/\eta) - \\ \{1 - \exp(-1/\eta^2)\} \cdot \eta/\sqrt{\pi} ]^2 \quad (3)$$

where $\tau = \sqrt{t/\theta}$ $\theta$ = Characteristic time of experiment = $d^2/k$ \quad (4)

The change in resistance of the square element due to the temperature increase $\overline{\Delta T(t)}$ is:

$$R(\tau) = R_o[1 + \alpha \cdot \overline{\Delta T}(\tau)] \quad (5)$$

where $\alpha$ = Temperature Coefficient of Resistivity
and if a constant current $I_o$ flows through the element then the changing voltage due to $\overline{\Delta T}(\tau)$ is $$U(\tau) = U_o \left[ 1 + \alpha \cdot \frac{P_o}{4d\Lambda \sqrt{\pi}} \cdot S(\tau) \right] \quad (6)$$

If the element is not embedded in the sample but makes contact with the sample on one side thereof, e.g. in form of a metal layer deposited on the sample, $P_o$ would go over to $2P_o$.

Equations (5) and (6) give the thermal properties of the sample substance if the function $S(\tau)$ could be evaluated. The function $S(\tau)$ is for small values of $\tau$ given by $$\lim_{\tau \to 0} S(\tau) = \tau - \frac{\tau^2}{\sqrt{\pi}} + \frac{\tau^3}{3\pi} \quad (7)$$

This approximation is valid $\tau < 0.4$. For $\tau$-values higher than 0,4 function $S(\tau)$ can be numerically evaluated and then approximated, e.g. by polynominals for different intervals of argument $\tau$.

Evaluation of U(t) as a function of time in a certain experiment is done in the same manner as in the THS-technique.

The characteristic time $\theta$ was iterated to give a maximum correlation r to the experimental points $(U(t_i), t_i)$ wherein r is defined by $$r = \frac{\Sigma_i[\{U(t_i) - \overline{U}\} \cdot \{S(\tau_i) - \overline{S}\}]}{\sqrt{\Sigma_i(U(t_i) - \overline{U})^2} \cdot \sqrt{\Sigma_i(S(\tau_i) - \overline{S})^2}} \quad (8)$$

where $\overline{U}$, $\overline{S}$ are average values of $U(t_i)$ and $S(\tau_i)$ resp. From the $\theta$-value giving maximum r the thermal diffusivity is found and using this $\theta$-value the slope of the best fit straight line to equation (6) would give the thermal conductivity, provided the temperature coefficient of resistivity $\alpha$ is known.

The electrical circuits used with the device according to the invention may be the same as those used in conventional THS-technique with an off-set arrangement or an unbalanced bridge.

The characteristic time $\theta$ of the experiment is much longer than in a normal THS experiment, because of the greater element width and hence the demand for time resolution is thus reduced, which facilitates the sampling the varying voltage.

Equation (3) above has been derived with the specific assumption that the total output of power in the Hot Square is constant and that all this power is consumed for heating the sample. However, for materials with low heat capacities per unit volume, which normally have very low thermal conductivities, it is not possible to neglect the heat capacity of the sensor used as Hot Square. From eq. (1) and (2) we can write:

$$\overline{\Delta T(t)} = \frac{1}{32\, d^2\, \pi^{3/2}} \int_o^t dt' \frac{\rho(t')}{[k(t-t')]^{3/2}} \int_{-d}^{d} dy \int_{-d}^{d} dy' \quad (9)$$

$$\exp[-(y-y')^2/4k(t-t')] \int_{-d}^{d} dz \int_{-d}^{d} dz' \exp[-(z-z')^2/4k(t-t')]$$

where $\rho(t) = [P_o - P_s(t)]/4\, d^2 \rho c$ $P_s(t) = 8\nu d^2 \rho_s\, c_s\, (d[\overline{\Delta T(t)}]/dt)$ 2 is the thickness and $\rho_s c_s$ is the heat capacity of the sensor used as Hot Square.

From solutions of eq. (9) it is obvious that eq. (3) can be used in all cases when $\rho_s c_s$ is of the same order of magnitude as $\rho c$ since the thickness (2) of the sensor can be made two or three orders of magnitude less than the side (2d) of the Hot Square.

However, for certain types of materials $\rho_s c_s$ might be orders of magnitude higher than $\rho c$ and in such cases it is necessary to use eq. (9) when evaluating a transient recording with the Hot Square or any other plane sensor.

As mentioned above the plane TPS elements may have different shapes and the electrical leads within the heated section of the element may be laid down in a large number of different ways (patterns) and still they fulfill the requirements of having approximately the same over-all size along two lateral dimensions. To illustrate this point we refer to the design in FIG. 7, which may be referred to as a Transient Hot Disc.

Assuming that the output of power ($P_o$) is constant, the average temperature increase $\overline{\Delta T(\tau)}$ of the thin coiled resistance strip of this element can be approximated by:

$$\overline{\Delta T(\tau)} = (P_o/a\Lambda)\, \pi^{-3/2} \int_o^\tau d\sigma\, \sigma^{-2} \int_o^1 v\, dv \int_o^1 u\, du \quad (10)$$

$$\exp[-(u^2 + v^2)/4\sigma^2]\, I_o(uv/2\sigma^2)$$

where a is the radius of the disc, $\Lambda$ is the thermal conductivity of the surrounding material, $I_o$ is a modified Bessel function, $\tau = (k\, t/a^2)^{\frac{1}{2}}$, k is the thermal diffusivity and t is the time measured from the initiation of the power release in the TPS element.

Equation (10) approximates the temperature increase in a element with a large number of concentric and circular heat sources arranged in such a way that the output of power per unit area can be considered constant over the entire disc.

Assuming that the hot disc consists of a specific number (n) of equally spaced concentric ring sources (Carslaw & Jaeger 1959), the mean temperature increase of the disc, as defined by equation (8) above, can be expressed as:

$$\overline{\Delta T(\tau)} = (P_o/a\,\Lambda)\, \pi^{-3/2}\, D(\tau) \quad (11)$$

where $$D(\tau) = \quad (12)$$

-continued $$[n(n+1)]^{-2} \int_o^\tau d\sigma\, \sigma^{-2} \left\{ \sum_{l=1}^{n} l \left[ \sum_{k=1}^{n} k \exp[-(l^2 + k^2)/4\sigma^2]\, I_o(lk/2\sigma^2)\right]\right\}$$

A detailed study of the difference between the two equations (10) and (11) shows that for $\tau$-values larger than say 0.1 and n larger than 15 the agreement between the two expressions can be made nearly perfect by applying a time correction. Since time corrections are being used as a standard procedure when evaluating all transient measurements, anyone of the two expressions can be used. However, because of difficulties to numerically approximate the integrals in equation (10), it is more convenient to use equations (11) and (12) to describe the behaviour of the hot disc.

When studying materials with low specific heat per unit volume a similar modification of the theory as demonstrated for the hot Square would apply also for the Hot Disc.

Emboidments in Practice

As the square strip according to the invention will give the great advantage of longer measuring times, the fact that the width is large and the length is equal to the width would imply that the initial resistance is low. This would require large currents for typical temperature increases of some degree in the strip. The design of a metal foil sensor with a higher initial resistance therefore is desirable, which could give longer measuring times and lower current. The most simple design of the invention is in form of a layer deposited by means of evaporation of a metal, e.g. nickel, directly on a sample if the sample is electrically non-conductive or has a thin layer of an electrically insulating material between the metal layer and the sample if this is electrically conductive. The resistance R of a square strip is $$R = \rho_{metal} \cdot \frac{1}{2\nu} \quad (13)$$

where $\rho_{metal}$ = electrical resistivity of the metal
$\nu$ = half thickness of the strip If the strip is constituted by a thin metal layer deposited on a substrate the initial resistance can be controlled rather easily. To reduce the effect of end contacts the embodiment according to FIGS. 2 and 3 can be used.

Two probe pads 2a and b, each having the width $\geq 4d$, the length $>4d$ and the thickness 2, where 2 is the thickness of the strip are deposited on the sample 3. These dimensions need not be exact, but the distance between the two probe pads should be exactly 2d. A strip 4 having the width 2d, the length $>2d$ and the thickness 2 is deposited transversally across the probe pads 2a and b, whereby the portions of the strip 4 projecting from the probe will overlap each probe pad 2a and b. Additional metal layers 5a and b are deposited on the probe pads 2a and b starting from their outer edges and over a length corresponding to e.g. d/3 for providing attachments for leads. However this length is not essential. It also should be pointed out that the thickness of the layers in FIG. 3 is heavily exaggerated for the sake of clarity.

It also is possible to deposit the metal layer before the probe pads if it is possible to avoid damages on the metal layer during changing of mask.

Figure 5:
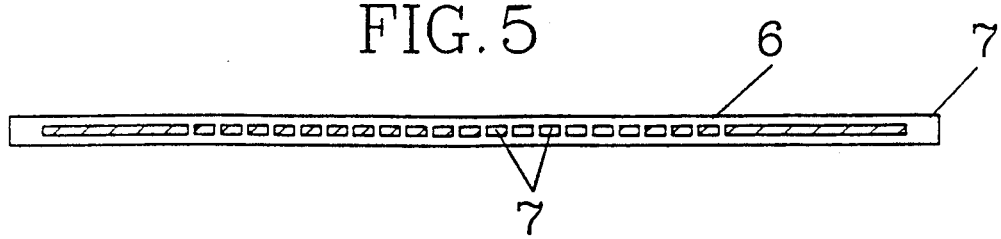
FIG. 5 is a section along line V—V in FIG. 4.

When using a metal foil, the initial resistance may be increased by etching away narrow strips of the metal foil with continued unbroken current path, such as shown in FIGS. 4 and 5. For increasing the mechanical strength of the sensor the top and bottom sides of the strip 6 are glued to a thin supporting material 7, such as kapton, in a manner similar to that used when producing flexible electronic circuits, heaters and strain gauges. The thickness of the layers is strongly exaggerated in FIG. 5 for the sake of clarity.

The etched away, empty spaces 8 are filled up by the supporting material 7 If the width of etched strip is $2\delta$ and the diffusivity of the insulation material, e.g. kapton 7 is $k_i$, then the time it would take for the temperature to become the same within the etched strip as in the unetched portion would be about $\delta^2/k_i$ and this TPS element should work as a true square heating a square section of the sample being tested and with the advantage of lower currents required.

The heat capacity of the insulating supporting material 7 has a significant influence when measuring on materials with low thermal conductivity. For materials having thermal conductivity bigger than, e.g. one magnitude higher than that of the insulating supporting material, this problem will be insignificant due to the long times of measurement.

The material in the metal foil 6 may be nickel or any other suitable conductor having a thickness of 10-15 $\mu$m, whereby the metal foil 6 is applied in a sandwich structure between two electrically insulating layers 7, e.g. of kapton, each having a thickness of about 15-25 $\mu$m. It also is possible to use thinner foil and insulating layers if it is possible to obtain sufficient mechanical strength. The overall thickness of the sensor would be about 70-100 $\mu$m, which includes the thickness of the insulating layers 7, the metal foil 6 and the bonding glue. Electric connections to current source and voltmeter (not shown) are joined to the metal foil 6 by soldering, pressure contacts etc.

The etching away of the foil produces, spatially, a number of strips n, each of a width of 2w and a length of 2h within the square 2h=2d. Said strips are parallel to each other, but electrically the strips are connected in series, which means a higher initial resistance. This means that if n is an even number then $$n(2w+2\delta)=2d$$

and which requires an etched away width of about $\delta$ on each side of the defined width 2d of the theoretical strip. Ideally $\delta$ would be very small and n very large, but from practical reasons the following dimensions are easy to obtain, etched away width $2\delta$ between 0.1 and 0.2 mm, $$(2w+2\delta)=1 \text{ mm}$$

and n = |2d|

The temperature range of the above TPS elements is essentially dependent on the materials used in the metal foil, insulating material and glue. The metal foil can be copper, nickel, silver, brass, platinum, tantalum etc. whereby the choice mainly is based on etching properties, mechanical strength and soldering properties for affixing the sensors. The insulating supporting material may be plastics, kapton, mica or sheets of powdered pressed mica etc. The choice is mainly based on mechanical strength, intended temperature range and required flexibility. Supporting materials which have high thermal conductivity and diffusivity are to be preferred. An advantage of the element according to the invention is that it may also be applied about curved sample surfaces.

The square element (d=h) according to the invention is applicable for materials having no direction dependency for the thermal properties. With corresponding technique it however is possible to design an element for which h>>d, which allows calculation of the direction dependency of the thermal properties.

Figure 6:
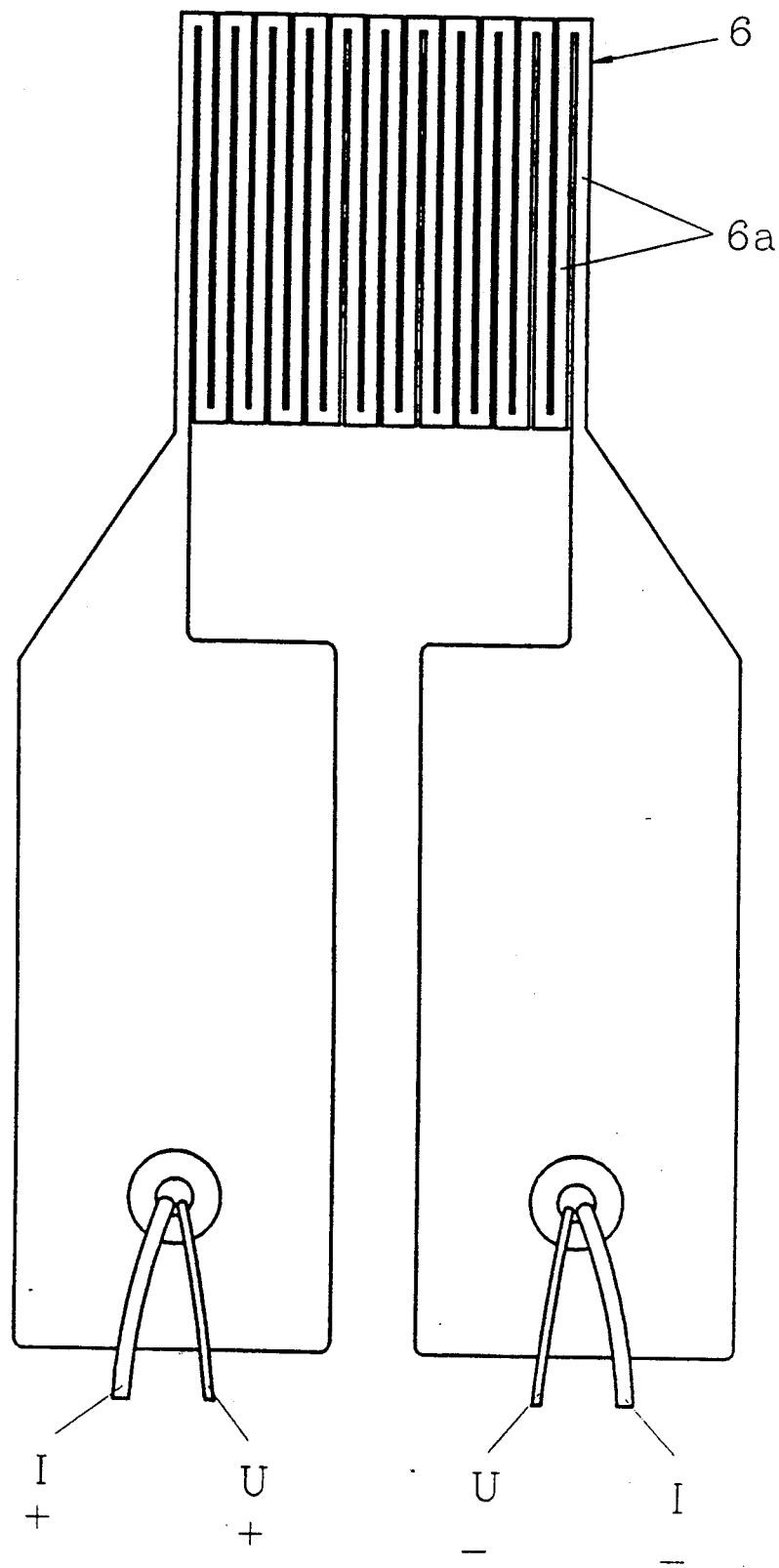
FIG. 6 shows in a view from above a third embodiment similar to FIG. 4.

In FIG. 6 there is shown another design of an element 6 comprising a resistive pattern of thin metal strips 6a arranged in a square pattern. The element 6 is preferably provided with insulating layers on each side of the resistive pattern.

In FIG. 7 is shown a further embodiment of an element 6 comprising a resistive pattern of thin metal strips 6a arranged in a circular pattern. The element is referred to above as a Transient Hot Disc. The radius of the disc is denoted a. The mathematical model on which the measurements with the Transient Hot Disc is based is given above.

Experimental Notes

One important aspect of the experimental technique is that the TPS element is placed between two pieces of the material to be tested. Each of these pieces must have one flat surface so that the element can be fitted closely between the pieces. The elements used so far have been manufactured with two insulating layers on each side of the resistive pattern, which makes it possible to use the elements also for measurements on electrically conducting materials.

Regarding the size of the pieces of material under test it is obvious that the distance from any part of the element to any of the free surfaces of the test piece should be at least $2(kt)^{\frac{1}{2}}$, which can be considered as the probing depth of the measurement. t is the total time of the transient recording.

If this condition is fulfilled we can safely use the theory developed above, which presumes that the element is placed in a material of infinite dimensions.

The new elements have so far been used for thermal conductivity and thermal diffusivity measurements on a large number of different materials with thermal conductivities ranging from 0.02 W/mK up to about 400 W/mK.

The temperature range covered so far extends from 80 to 900 Kelvin. The accuracy of these measurements is typically around one percent.

Deviation from the Mathematical Model

There are deviations from the mathematical model that must be considered:
a. influence from the leads carrying the current to the strip pattern that makes up the TPS element
b. influence from the openings within the strip pattern
c. lateral heat flow in the element when studying material with low thermal conductivity Influence from the leads can be made negligably small if the design of the FIG. 4 is used. However, this design cannot be used for materials with very low thermal conductivity because of the lateral heat flow inside the element itself.

For low conducting materials the strip-pattern designs of FIGS. 6 and 7 have proven very good, since the lateral heat flow is negligible.

The slight deviation from the mathematical model of the elements depicted in FIGS. 6 and 7 is related to heat discipation over a short section of the current leads outside the hot Square or Hot Disc. However, with the proposed design this output of power can be made as small as a fraction of a percent of the total output of power.

Regarding the small openings in the strip pattern within each of the elements, the particular design must be such that the total time of the transient recording, which typically is about $d^2/k$ or $a^2/k$ must be several orders of magnitude larger than $\delta^2/k_i$, where $\delta$ is the lateral size of the opening between the strips and $k_i$ is the thermal diffusivity of the material filling out the opening.

It is obvious that this condition is rather easy to fulfill since the $d/\delta$ ratio can be made as high as 100 with d typically around 10 mm.

In the experimental studies performed so far no influence from the openings in the resistive pattern has been recorded.

It is also possible to solve the thermal conductivity equation exactly for any type of pattern. This would normally require a numerical evaluation of the integrals, which preferably are expressed as a function of $\tau$.

The invention is of course not limited to the embodiments described above and shown in the drawings, but can be modified within the scope of the claims.

I claim:

1. A device for measuring thermal properties of a test substance, which device incorporates a thin element or a layer of an electrically conductive material, e.g. metal, intended to be brought in heat conductive contact with said test substance, means for passing an electric current through said element or layer for supplying heat to the test substance and causing a temperature increase therein and means for recording the voltage variation over the element or the layer as a function of time and to evaluate therefrom thermal properties, such as thermal conductivity thermal diffusivity and specific heat per unit volume of the test substance, wherein the active part of said element or layer has substantially equal size along at least two lateral dimensions.

2. A device as claimed in claim 1, wherein the active part of said element or layer has a substantially square configuration.

3. A device as claimed in claim 1, wherein the active part of said element or layer has a substantially circular configuration.

4. A device as claimed in claim 1, wherein the element comprises a metal foil with etched away, narrow and mainly parallel strips with maintained unbroken current path past the strips, that the metal foil is fixed between thin layers of an electric insulating supporting material, and that the portion of the metal foil forming the current path through the etched portion of the metal foil has mainly the same length and width.

5. A device as claimed in claim 1, wherein it comprises a layer deposited directly upon the test substance or via an intermediate thin layer of an electrically insulating material of said electrically conducting material, e.g. metal.

6. A device as claimed in claim 5, wherein it incorporates a pair of probe pads having a length and a width exceeding the active width of the layer fitted directly against the test substance at a mutual distance corresponding to the active width of the layer, which layer has a length exceeding the width and is arranged between the probe pads with a portion of the projecting length overlapping each probe pad.

7. A device as claimed in claim 6, wherein additional metal layers are arranged on the free portions of said probe pads for forming electrical connections.

* * * * *